US00PP13869P39

(12) United States Plant Patent
Noack

(10) Patent No.: US PP13,869 P3
(45) Date of Patent: Jun. 10, 2003

(54) GROUND COVER ROSE PLANT NAMED 'NOALESA'

(76) Inventor: Reinhard Noack, Im Fenne 54, 33334 Gütersloh (DE)

( * ) Notice: Subject to any disclaimer, the term of this patent is extended or adjusted under 35 U.S.C. 154(b) by 0 days.

(21) Appl. No.: 09/843,756

(22) Filed: Apr. 30, 2001

(65) Prior Publication Data

US 2002/0062508 P1 May 23, 2002

(51) Int. Cl.[7] ..... A01H 5/00
(52) U.S. Cl. ..... Plt./104
(58) Field of Search ..... Plt./104, 102, 141, Plt./145

(56) References Cited

PUBLICATIONS

UPOV–ROM GTITM Computer Database 2001/06, GTI Jouve Retrieval Software, Citation for Rosa 'Noalesa'.*
Blatt Für Sortenwesen Amtsblatt Des Bundessortenamtes, No. 1, Jan. 15, 2001 Cover Page and p. 13.

* cited by examiner

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

A new and distinct variety for Ground Cover Rose plant is provided which forms substantially continuously throughout the season attractive long-lasting bright yellow blossoms. The blossoms open on a reliable bases and retain their attractiveness upon aging. The new variety exhibits a compact, spreading and overhanging growth habit that renders it suitable for growing as attractive ornamentation in the landscape. The foilage is glossy and dark green and contrasts well with the bright yellow blossoms. The blossom petals detach cleanly as the blossoms mature. The new variety propagates well by the use of cuttings, and by budding and grafting. Excellent resistance to Blackspot, Powdery Mildew, and Rust is exhibited.

2 Drawing Sheets

BOTANICAL/COMMERCIAL CLASSIFICATION

*Rosa hybrida*/Ground Cover Rose Plant.

VARIETAL DENOMINATION cv. Noalesa.

SUMMARY OF THE INVENTION

Ground Cover rose plants are known and are being used to advantage in an increasing number of landscape plans and home gardens. However, there remains a need for additional varieties of Ground Cover roses with the demand being the greatest for those having highly attractive blossoms in combination with good disease resistance.

The new variety of *Rosa hybrida* Ground Cover rose plant of the present invention was created at Gütersloh, Germany, by artificial pollination wherein two parents were crossed which previously had been studied in the hope that they would contribute the desired characteristics. The female parent (i.e., the seed parent) was the 'Korimro' variety (non-patented in the United States). Such 'Korimro' variety possesses light pink to near white single blossoms and is marketed under the IMMENSEE trademark. The male parent (i.e., the pollen parent) was an unnamed seedling maintained by Noack Rosen at Gütersloh, Germany (non-patented in the United States). The parentage of the new variety can be summarized as follows:

'Korimro'×Unnamed Seedling.

The seeds resulting from the above pollination were sown and small plants were obtained which physically and biologically differ from each other. Selective study resulted in the identification of a single plant to the new variety.

It is found that the new variety of Ground Cover rose plant possesses the following combination of characteristics:

(a) Forms attractive bright yellow blossoms,
(b) Young plants exhibit an upright growth habit that becomes spreading, dense, and compact with maturity,
(c) Forms attractive dark green glossy foliage that contrasts well with the bright yellow blossoms,
(d) Exhibits excellent disease resistance with respect to Blackspot, Powdery Mildew, and Rust, and
(e) Is particularly well suited for growing as attractive ornamentation in the landscape.

The new variety meets the needs of the horticultural industry and can be grown to advantage as attractive ornamentation in parks, gardens, public areas, and residential landscapes.

The new variety of the present invention beginning in 1994 has been asexually reproduced by the rooting of cuttings, by budding, and by grafting. Such asexual reproduction as performed at Gütersloh, Germany, has demonstrated that the characteristics of the new variety are firmly fixed and stable and are strictly transmissible from one generation to another.

The new variety has been named the 'Noalesa', and recently has been marketed abroad under the JACOBS KR ÖNUNG trademark.

BRIEF DESCRIPTION OF THE PHOTOGRAPHS

The accompanying photographs show as nearly true as it is reasonably possible to make the same, in color illustrations of this character, typical specimens of the new variety while growing in the landscape. The illustrated rose plants were photographed during July, 1996, while growing in the field at Gütersloh, Germany. Such plants were budded approximately one and one-half years earlier.

DETAILED DESCRIPTION

The chart used in the identification of the colors is that of The Royal Horticultural Society (R.H.S. Colour Chart) of London, England. Color terminology in common terms sometimes is included as an aid to the reader. Such terminology is to be accorded its customary dictionary significance. The description is based on the observation of specimens of the new variety while growing outdoors during July at Gütersloh, Germany.

Class: Ground Cover.

Parentage:

*Female.*—'Korimro' (non-patented in the United States).

*Male.*—Unnamed Seedling maintained by Noack Rosen at Gütersloh, Germany (non-patented in the United States).

Plant:

*Form.*—Vigorous, young plants exhibit an upright growth habit, then as the plant matures they spread to form a compact bush that serves well as ground cover with dense foliage.

Branches:

*Color.*—Young stems: Green Group 135C and slightly reddish, and with a smooth surface. Adult wood: Green Group 135B and a little darker than the young stems, and with a smooth surface.

*Thorns.*—Size: medium, approximately 5 mm in length on average, and slightly curved downward, and concave on the under surface. Position: irregular. Color: initially Greyed-Orange Group 163D and changing to Greyed-Orange Group 162B with maturity. Quantity: moderate and typical for a Ground Cover rose plant.

Leaves:

*Stipules.*—Green Group 139B in coloration, and approximately 1 cm in length.

Figure 1:
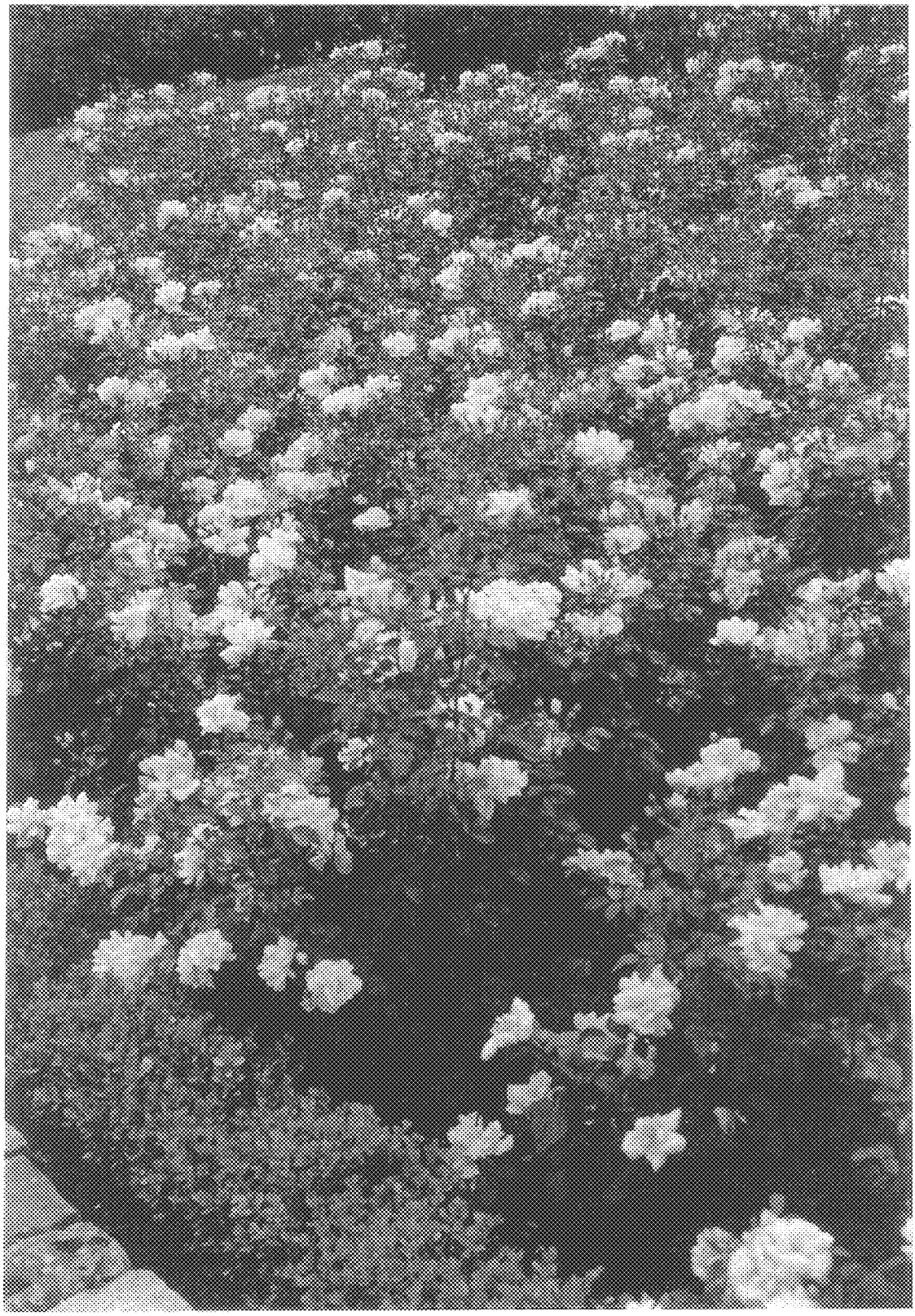
FIG. 1 illustrates the overall appearance of typical plants of the new variety while bearing a profusion of blossoms in various stages of opening.
Figure 2:
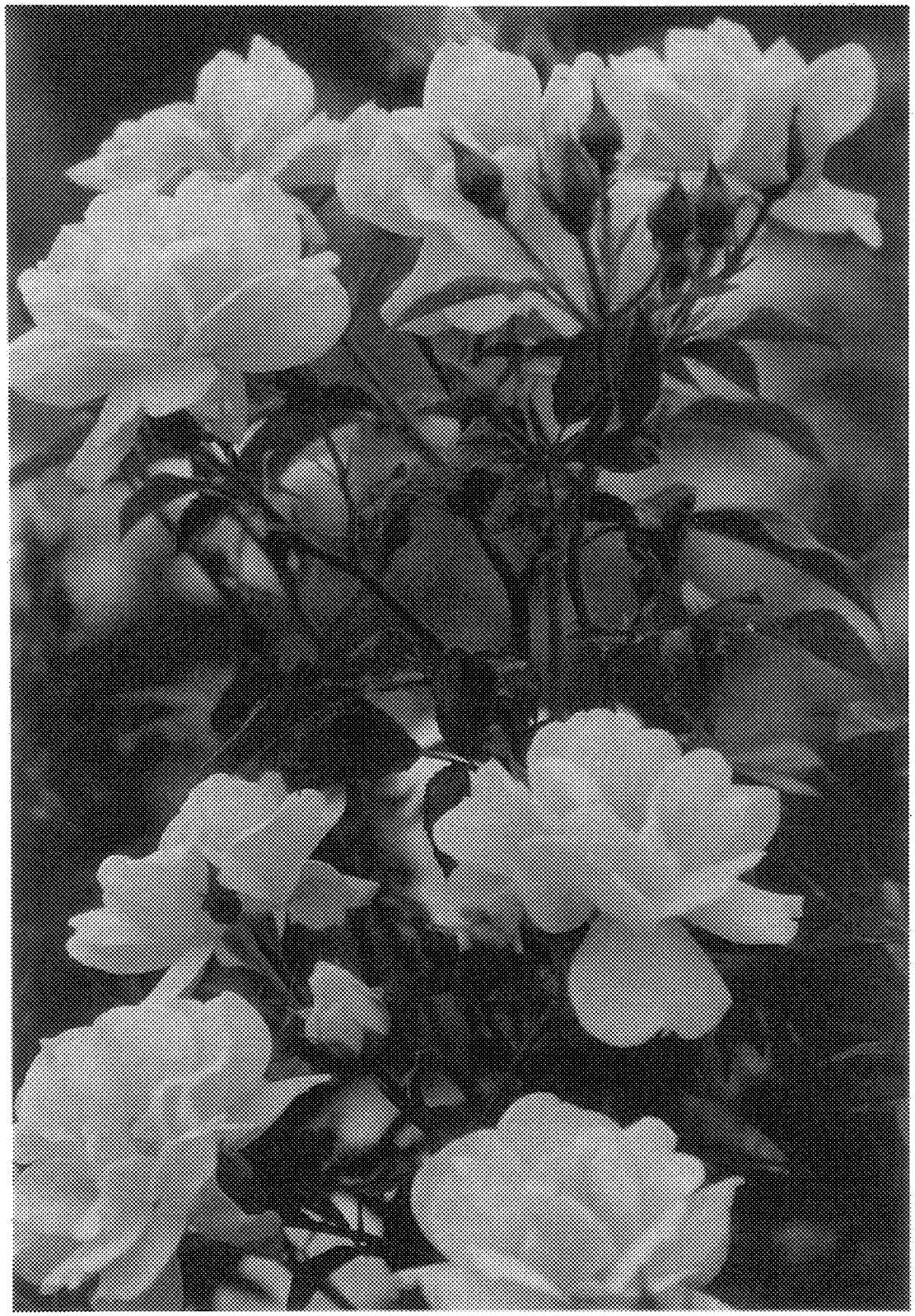
FIG. 2 illustrates a closer view of typical blossoms, buds, and foliage of the new variety wherein the bright yellow blossoms are shown to contrast nicely with the glossy dark green foliage.

*Leaflets.*—Number: commonly 5 and 7. Configuration: elliptical, concave and pointed. Quantity: very abundant. Size: the terminal leaflet commonly is approximately 4 cm in length and approximately 3 cm in width. Serration: slightly serrate, as illustrated in FIG. 2. Color: (young foliage): upper surface: Green Group 143A. under surface: Green Group 143C. Color: (adult foliage): upper surface: Green Group 132A. under surface: Green Group 132C. General appearance: dense, dark green foilage that is glossy on the upper surface and matte on the under surface. Texture: leathery. Petiole: smooth and glossy.

Inflorescence:

*Number of flowers.*—In clusters of approximately 15 to 20 flowers in a large spray.

*Peduncle.*—Green Group 139B in coloration, and smooth.

*Sepals.*—Shape: smooth, pointed as illustrated in FIG. 2, Greyed-Green Group 198A in coloration, approximately 1 to 1.5 cm in length, and commonly bear pointed extensions.

*Buds.*—Length: approximately 3 cm on average. Color when opening: Mimosa Yellow, Yellow Group 8A to 8C.

*Flower.*—Form: initially cup-shaped with flattening upon maturity. Appearance: smooth and somewhat satiny on both petal surfaces. Diameter: 5 cm on average. Color (when opening begins): upper surface: Mimosa Yellow, predominantly Yellow Group 8A. Under surface: Mimosa Yellow, predominantly Yellow Group 8A to 8C. Color (when blooming): upper surface: Mimosa Yellow, predominantly Yellow Group 8B. The yellow coloration of pollen and reproductive organs commonly is also visible. under surface: Mimosa Yellow, predominantly Yellow Group 8A to 8C. Color (at the end of opening): upper surface: Mimosa Yellow, near Yellow Group 8D with some variation in color. under surface: Mimosa Yellow, Yellow Group 8A to 8C. Basal color spot: none observed during observations to date. Petal number: commonly approximately 15 per flower. Fragrance: slight. Lasting quality: very good. Petal form: broad, fan-shaped, curved with a lightly indented central area and margin areas that are slightly curved towards the center. Petal size: approximately 3 cm in length and approximately 2 cm in width. Petaloids: none observed during observations to date. Petal arrangement: generally arranged in a regular pattern with overlapping edges. Lastingness: commonly last approximately 5 to 7 days depending upon the environment. Petal drop: good with the petals detaching cleanly. Stamens: regularly arranged around the style. Filaments: approximately 1 cm in length, regularly arranged around the style, Yellow-Orange Group 22B in coloration, and are nearly transparent in appearance. Anthers: approximately 3 mm in size. Pollen: light yellow in coloration. Stigmas: Yellow-Orange Group 21A in coloration. Styles: thin, approximately 1.3 cm in length, regularly arranged at the center, and Yellow-Orange Group 21A in coloration. Hips: cup-shaped, smooth, approximately 1 to 1.5 cm in length, and upon maturity change from Green Group 137C to Red Group 44B in coloration.

Development:

*Vegetation.*—Strong and vigorous.

*Blooming.*—Abundant in sprays.

*Aptitude to bear fruit.*—Slight.

*Winter hardiness.*—Good and comparable to that of the 'Flower Carpet Pink' variety (U.S. Plant Pat. No. 7,282).

*Resistance to diseases.*—Excellent with respect to Blackspot, Powdery Mildew, and Rust.

I claim:

1. A new and distinct variety of Ground Cover Rose plant characterized by the following combination of characteristics:

(a) Forms attractive bright yellow blossoms, (b) Young plants exhibit an upright growth habit that becomes spreading, dense, and compact with maturity, (c) Forms attractive dark green glossy foilage that contrasts well with the bright yellow blossoms, (d) Exhibits excellent disease resistance with respect to Blackspot, Powdery Mildew, and Rust, and (e) Is particularly well suited for growing as attractive ornamentation in the landscape;

substantially as herein shown and described.

* * * * *